United States Patent
Manzer

(10) Patent No.: US 7,030,249 B2
(45) Date of Patent: Apr. 18, 2006

(54) PROCESS FOR CONVERTING α-ANGELICA LACTONE TO 5-METHYL-N-ALKYL-2-PYRROLIDONE USING ALKYL AMINES

(75) Inventor: Leo Ernest Manzer, Wilmington, DE (US)

(73) Assignee: E. I. uPont de Nemours and Company, Wilmington, DE (US)

( * ) Notice: Subject to any disclaimer, the term of this patent is extended or adjusted under 35 U.S.C. 154(b) by 19 days.

(21) Appl. No.: 10/936,985

(22) Filed: Sep. 8, 2004

(65) Prior Publication Data

US 2005/0054861 A1 Mar. 10, 2005

Related U.S. Application Data

(60) Provisional application No. 60/501,686, filed on Sep. 10, 2003.

(51) Int. Cl.
*C07D 207/40* (2006.01)
(52) U.S. Cl. ...................................... 548/545; 549/266
(58) Field of Classification Search ................ 548/545; 549/266
See application file for complete search history.

(56) References Cited

U.S. PATENT DOCUMENTS 2,809,203 A 10/1957 Leonard
3,235,582 A 2/1966 Shilling

OTHER PUBLICATIONS

C. Wedler et al, Synthesis of 5-Methyl- and 5-Methylenepyrrolidin-2-ones by Reaction of α-Angelica Lactone with Methylamine, Journal für Praktische Chemie, vol. 332, No. 4, 1990, pp. 557-562 (XP008039370).
Paitoon Rashatasakhon et al., The Reaction of Cyclic Carbinol Amides with Triflic Anhydride as a Method to Prepare α-Trifluoromethyl-Sulfonamido Furans, Organic Letters, vol. 5, No. 2, 2003 pp. 189-191 (XP002307750).

*Primary Examiner*—Kamal A. Saeed
(74) *Attorney, Agent, or Firm*—Gerald E. Deitch

(57) ABSTRACT

This invention relates to a process for producing 5-methyl-N-alkyl-2-pyrrolidone by a) reacting α-angelica lactone with alkyl amines and b) hydrogenating the products of step (a) in the presence of a metal catalyst, which is optionally supported.

15 Claims, No Drawings

PROCESS FOR CONVERTING α-ANGELICA LACTONE TO 5-METHYL-N-ALKYL-2-PYRROLIDONE USING ALKYL AMINES

CROSS REFERENCE TO RELATED APPLICATIONS

This application claims priority under 35 U.S.C. §119 from U.S. Provisional Application Ser. No. 60/501,686, filed Sep. 10, 2003.

FIELD OF INVENTION

This invention relates to a process for producing 5-methyl-N-alkyl-2-pyrrolidone by a) reacting α-angelica lactone with alkyl amines and b) hydrogenating the products of step (a) in the presence of a metal catalyst, which is optionally supported.

BACKGROUND OF THE INVENTION

N-Alkyl-pyrrolidones can act as solvents, surfactants, dispersants, detergents and emulsifiers, and thus are useful in a wide variety of applications. N-Alkyl-pyrrolidones are components, for example, in cleaners such as industrial, metal and surface cleaners, paint strippers, printing inks, gasoline and oil additives, industrial coatings and detergents. N-Alkyl-pyrrolidones are also useful in oil and gas well maintenance, polymer synthesis, photoresist applications, agricultural and pharmaceutical manufacture and paper manufacture.

Angelica lactone can be prepared from renewable resources (U.S. Pat. No. 2,809,203) and represents a novel, low cost starting material for the production of N-alkyl-pyrrolidones.

Wedler, et al. (Journal. f. prakt. Chemie (1990) 332: 557–562) discuss a process for producing 5-hydroxy-1,5-dimethyl-2-pyrrolidone by reacting α-angelica lactone with methylamine. Dehydration of this product resulted in the formation of the unstable 5-methylene-N-methyl-2-pyrrolidone, rather than the desired 1,5-dimethyl-2-pyrrolidone.

An efficient and low cost process for the production of diverse alkyl pyrrolidones would be advantageous.

SUMMARY OF THE INVENTION

The present invention relates to a novel, two-step process for converting α-angelica lactone to 5-methyl-N-alkyl-2-pyrrolidone. The process comprises the steps of a) contacting α-angelica lactone with an alkyl amine, optionally in the presence of an inert solvent, and b) reacting the products of step (a) with hydrogen gas and a catalyst, the catalyst being optionally supported on a catalyst support;

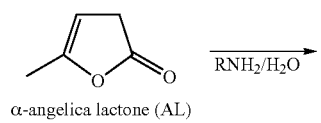
α-angelica lactone (AL)

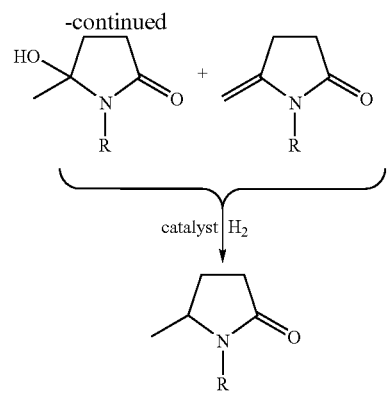

to produce 5-methyl-N-alkyl-2-pyrrolidone, wherein R is selected from the group consisting of $CH_3$, $C_2H_5$, straight-chain or branched $C_3$ to $C_{30}$ alkyl, and straight-chain or branched $C_3$ to $C_{30}$ alkyl comprising a heteroatom selected from the group consisting of O and N.

The catalyst useful in the process of the invention is selected from metals selected from the group consisting of nickel, copper, cobalt, iron, rhodium, ruthenium, rhenium, osmium, iridium, platinum, palladium, at least one Raney® metal; compounds thereof; and combinations thereof. A catalyst support may be optionally used.

The molar ratio of $RNH_2$ to α-angelica lactone is from about 1/1 to about 1.5/1 at the start of the reaction. According to the process of the invention, step (a) is performed at a temperature of from about −25° C. to about 50° C., and step (b) is performed at a temperature of from about 50° C. to about 300° C.; step (b) of the reaction is performed at a hydrogen pressure of from about 0.1 MPa to about 20 MPa.

DETAILED DESCRIPTION OF THE INVENTION

By "5-methyl-N-alkyl-2-pyrrolidone" is meant the compound having the general formula below wherein R is selected from the group consisting of $CH_3$, $C_2H_5$, straight-chain or branched $C_3$ to $C_{30}$ alkyl, and straight-chain or branched $C_3$ to $C_{30}$ alkyl comprising a heteroatom selected from the group consisting of O and N:

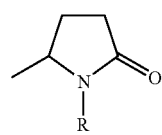

By "alkyl" is meant a monovalent radical having the general formula $C_nH_{2n+1}$.

By "catalyst" is meant a substance that affects the rate of the reaction but not the reaction equilibrium, and emerges from the process chemically unchanged.

By "metal catalyst" is meant a catalyst that is comprised of at least one metal, at least one Raney® metal, compounds thereof or combinations thereof.

By "promoter" is meant an element of the Periodic Table that is added to enhance the physical or chemical function of the catalyst. The promoter can also be added to retard undesirable side reactions and/or affect the rate of the reaction.

By "metal promoter" is meant a metallic compound that is added to enhance the physical or chemical function of a catalyst. The metal promoter can also be added to retard undesirable side reactions and/or affect the rate of the reaction.

The present invention relates to a process for preparing 5-methyl-N-alkyl-2-pyrrolidone. This two-step process comprises the steps of a) contacting α-angelica lactone with an alkyl amine, optionally in the presence of an inert solvent, and b) reacting the products of step (a) with a catalyst in the presence of hydrogen gas to produce 5-methyl-N-alkyl-2-pyrrolidone:

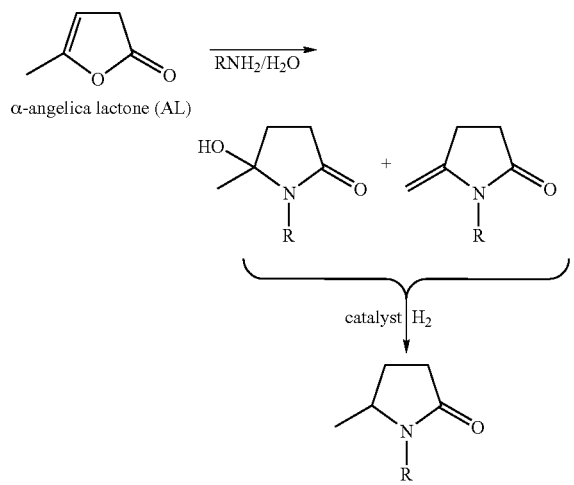

α-angelica lactone (AL)

wherein R is selected from the group consisting of $CH_3$, $C_2H_5$, straight-chain or branched $C_3$ to $C_{30}$ alkyl, and straight-chain or branched $C_3$ to $C_{30}$ alkyl comprising a heteroatom selected from the group consisting of O and N.

A catalyst, with or without a support, may be present in the process of the invention to effect the hydrogenation reaction. A promoter may optionally be used to aid the reactions. The promoter can be a metal.

The process of the present invention may be carried out in batch, sequential batch (i.e., a series of batch reactors) or in continuous mode in any of the equipment customarily employed for continuous processes (see for example, H. S. Fogler, Elementary Chemical Reaction Engineering, Prentice-Hall, Inc., New Jersey, USA).

In one embodiment of the invention, R is selected from the group consisting of $CH_3$, $C_2H_5$, straight-chain or branched $C_3$ to $C_{18}$ alkyl, and straight-chain or branched $C_3$ to $C_{18}$ alkyl comprising a heteroatom selected from the group consisting of O and N. In another embodiment of the invention, R is selected from the group consisting of $CH_3$, $C_2H_5$, straight-chain or branched $C_3$ to $C_{12}$ alkyl, and straight-chain or branched $C_3$ to $C_{12}$ alkyl comprising a heteroatom selected from the group consisting of O and N.

In one embodiment of the invention, a molar ratio of alkyl amine to α-angelica lactone is from about 0.1/1 to about 10/1 at the start of the reaction; in another embodiment, the molar ratio of alkyl amine to α-angelica lactone is from about 1/1 to about 1.5/1 at the start of the reaction.

A temperature range of from about −25° C. to about 50° C. is preferred for the amination reaction of step (a). A temperature range of from about 50° C. to about 300° C. is preferred for the hydrogenation reaction of step (b) of the invention. A temperature range of from about 100° C. to about 250° C. is further preferred for step (b) of the reaction.

A pressure range of from about 0.1 MPa to about 20 MPa is employed for the processes of the invention. A pressure range of from about 1.3 MPa to about 7.6 MPa is preferred.

The reactions of the present invention can be performed in a suitable inert solvent. An inert solvent is a solvent that does not participate in the reactions of the present invention and does not adversely affect the reactants or products. Suitable inert solvents include water and ethers, such as dioxane. Alternatively, the excess of alkyl amine can also act as the solvent medium.

The catalyst useful in the invention is a substance that affects the rate of the reaction but not the reaction equilibrium, and emerges from the process chemically unchanged. A chemical promoter may augment the activity of a catalyst. The promoter herein may be incorporated into the catalyst during any step in the chemical processing of the catalyst constituent. The chemical promoter generally enhances the physical or chemical function of the catalyst agent, but can also be added to retard undesirable side reactions.

The hydrogenation reaction of the invention may be effected in the presence of a catalyst. The principal component of the catalyst useful herein is selected from metals from the group consisting of palladium, ruthenium, rhenium, rhodium, iridium, platinum, nickel, cobalt, copper, iron, osmium; compounds thereof; and combinations thereof.

A promoter may be used optionally in the hydrogenation reaction of the present invention. Suitable promoters include metals selected from tin, zinc, copper, gold, silver, and combinations thereof. The preferred metal promoter is tin. Other promoters that can be used are elements selected from Group 1 and Group 2 of the Periodic Table.

The catalyst used in the hydrogenation reaction may be supported or unsupported. A supported catalyst is one in which the active catalyst agent is deposited on a support material by a number of methods, such as spraying, soaking or physical mixing, followed by drying, calcination, and if necessary, activation through methods such as reduction or oxidation. Materials frequently used as a support are porous solids with high total surface areas (external and internal), which can provide high concentrations of active sites per unit weight of catalyst. The catalyst support may enhance the function of the catalyst agent. A supported metal catalyst is a supported catalyst in which the catalyst agent is a metal.

A catalyst that is not supported on a catalyst support material is an unsupported catalyst. An unsupported catalyst may be platinum black or a Raney® catalyst. Raney® catalysts have a high surface area due to selectively leaching an alloy containing the active metal(s) and a leachable metal (usually aluminum). Raney® catalysts have high activity due to the higher specific area and allow the use of lower temperatures in hydrogenation reactions. The active metals of Raney® catalysts include nickel, copper, cobalt, iron, rhodium, ruthenium, rhenium, osmium, iridium, platinum, palladium; compounds thereof; and combinations thereof.

Promoter metals may also be added to the base Raney® metals to affect selectivity and/or activity of the Raney® catalyst. Promoter metals for Raney® catalysts may be selected from transition metals from Groups IIIA through VIIIA, IB and IIB of the Periodic Table of the Elements. Examples of promoter metals include chromium, molybdenum, platinum, rhodium, ruthenium, osmium, and palladium, typically at about 2% by weight of the total metal.

The catalyst support useful herein can be any solid, inert substance including, but not limited to, oxides such as silica, alumina and titania; barium sulfate; calcium carbonate; and carbons. The catalyst support can be in the form of powder, granules, pellets, or the like.

A preferred support material of the invention is selected from the group consisting of carbon, alumina, silica, silica-alumina, silica-titania, titania, titania-alumina, barium sulfate, calcium carbonate, strontium carbonate, compounds thereof and combinations thereof. Supported metal catalysts can also have supporting materials made from one or more compounds. More preferred supports are alumina, silica, titania and carbon. Further preferred supports are carbons with a surface area greater than 100 m²/g. A further preferred support is carbon with a surface area greater than 200 m²/g. Preferably, the carbon has an ash content that is less than 5% by weight of the catalyst support; the ash content is the inorganic residue (expressed as a percentage of the original weight of the carbon) which remains after incineration of the carbon.

Commercially available carbons which may be used in this invention include those sold under the following trademarks: Bameby & Sutcliffe™, Darco™, Nuchar™, Columbia JXN™, Columbia LCK™, Calgon PCB™, Calgon BPL™, Westvaco™, Norit™ and Barnaby Cheny NB™. The carbon can also be commercially available carbon such as Calsicat C, Sibunit C, or Calgon C (commercially available under the registered trademark Centaur®).

In the processes of the invention, the preferred content of the metal catalyst in the supported catalyst is from about 0.1% to about 20% of the supported catalyst based on metal catalyst weight plus the support weight. A more preferred metal catalyst content range is from about 1% to about 10% of the supported catalyst. A further preferred metal catalyst content range is from about 3% to about 7% of the supported catalyst.

Combinations of catalyst and support system may include any one of the metals referred to herein with any of the supports referred to herein. Preferred combinations of catalyst and support include palladium on carbon, palladium on calcium carbonate, palladium on barium sulfate, palladium on alumina, palladium on silica, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, rhenium on alumina, ruthenium on carbon, ruthenium on alumina, ruthenium on silica and combinations thereof.

Further preferred combinations of catalyst and support include palladium on carbon, palladium on alumina, palladium on silica, palladium on titania, platinum on carbon, platinum on alumina, platinum on silica, iridium on silica, iridium on carbon, iridium on alumina, rhodium on carbon, rhodium on silica, rhodium on alumina, nickel on silica, ruthenium on carbon, ruthenium on alumina, ruthenium on silica and combinations thereof. A further preferred combination is palladium on carbon.

The following examples are illustrative of the invention.

EXAMPLES

The following abbreviations are used:
ESCAT-XXX: Series of catalysts provided by Engelhard Corp. (Iselin, N.J.)
JM-XXXX: Series of catalysts from Johnson Matthey, Inc. (W. Depfford, N.J.)
ST-XXXX-SA: Series of catalysts from Strem Chemicals (Newburyport, Mass.)

Calsicat Carbon: Catalyst support from Engelhard Corp. (lot S-96-140)
SCCM: Standard cubic centimeters per minute
GC: Gas chromatography
GC-MS: Gas chromatography-mass spectrometry For catalyst preparation a commercially available support such as carbon, alumina, silica, silica-alumina or titania was impregnated by incipient wetness with a metal salt. The catalyst precursors used were $Re_2O_7$ (Alfa Chemical Co.), $PdCl_2$ (Alfa Chemical Co.), $RuCl_3 \cdot xH_2O$ (Aldrich Chemical Co., Milwaukee, Wis.), $H_2PtCl_6$ (Johnson Matthey, Inc.) and $RhCl_3 \cdot xH_2O$ (Alfa Chemical Co.). The samples were dried and reduced at 300–450° C. under $H_2$ for 2 hours.

α-Angelica lactone and methylamine are available from Fisher Scientific (Chicago, Ill.).

Catalyst Preparation: 5% Pt on Acid Washed Calsicat Carbon

In a 150 ml beaker, a solution was made up of 4.5 ml 0.3 M $H_2PtCl_6$ with 4.0 ml deionized $H_2O$. To the beaker were added 4.75 g Calsicat Acid Washed Carbon (12×20 mesh, dried at 120° C. overnight). The slurry was allowed to stand at room temperature for 1 hr with occasional stirring, followed by drying at 120° C. overnight with frequent stirring (until free flowing).

In an alumina boat, in a quartz lined tube furnace, the catalyst was purged with 500 SCCM $N_2$ at room temperature for 15 min and then with 100 SCCM He at room temperature for 15 min. The catalyst was heated to 150° C. and held at 150° C. under He for 1 hr. At this point, 100 SCCM $H_2$ were added and the sample was held at 150° C. under He and $H_2$ for 1 hr. The temperature was increased to 300° C. and the catalyst was reduced at 300° C. under He—$H_2$ for 8 hrs. The $H_2$ was stopped, the sample was held at 300° C. under He for 30 min and then cooled to room temperature in flowing He. The catalyst was finally passivated in 1.5% $O_2$ in $N_2$ at 500 SCCM for 1 hr at room temperature and weighed 4.93 g when unloaded.

Additional catalysts used in the present invention were prepared following a similar procedure.

Preparation of 1,5-Dimethyl-2-Pyrrolidone

The first part of the process consisted of reacting α-angelica lactone (AL) with methylamine (MA) (as a solution containing 55.6 wt. % AL and 44.4% of an aqueous solution of MA (40 wt. % MA in water); 495.2 mg total) at room temperature for 5–600 minutes. The AL/MA solution was then placed in a pressure vessel and 51.4 mg of catalyst (5% Pd/C) was added. The vessel was sealed, charged with 5.52 MPa hydrogen and heated to 100° C. for 2 hours. The pressure was maintained at 5.52 MPa during the course of the reaction. At the end of the reaction, the vessel was rapidly cooled in ice, vented and an internal GC standard of methoxyethylether was added. The solution was separated by pipette from the catalyst and analyzed by GC-MS using an HP 6890 (Agilent; Palo Alto, Calif.) equipped with a FFAP 7717 (30 meter) column. The results set forth in the tables below are based on area %.

The examples described below were performed according to a similar procedure under the conditions indicated for each example.

Examples 1–5

Preparation of 1,5-Dimethyl-2-Pyrrolidone (DMP) by Amination of α-Angelica Lactone (AL) with Methylamine (MA) and Hydrogenation of the Products The feedstock for the reaction was 55.6 wt. % AL/44.4 wt. % of aqueous MA (40 wt. % MA in water). The amination reaction was carried out at room temperature for 60 minutes; the hydrogenation reaction was carried out for 2 hr at a temperature and pressure of 100° C. and 5.52 MPa, respectively.

| Ex. No. | Catalyst/Support[a] | Catalyst/ Support (mg) | Feed- stock (mg) | AL Conversion (%) | DMP Selectivity (%) |
|---|---|---|---|---|---|
| 1 | 5% Pd/C (ESCAT-142) | 51.4 | 495.2 | 90.95 | 74.23 |
| 2 | 5% Pt/C (ESCAT-248) | 51.2 | 495.9 | 52.04 | 52.38 |
| 3 | 5% Ru/C (ST-141060-SA) | 48.2 | 493 | 77.57 | 48.81 |
| 4 | 5% Rh/C (JM-11761) | 50.7 | 516.1 | 79.68 | 88.20 |
| 5 | 5% Re/C (Acros) | 50.4 | 495 | 22.91 | <1% |

What is claimed is:

1. A process comprising the steps of a) contacting α-angelica lactone with an alkyl amine, optionally in the presence of an inert solvent, and b) reacting the products of step (a) with hydrogen gas and a catalyst, the catalyst being optionally supported on a catalyst support;

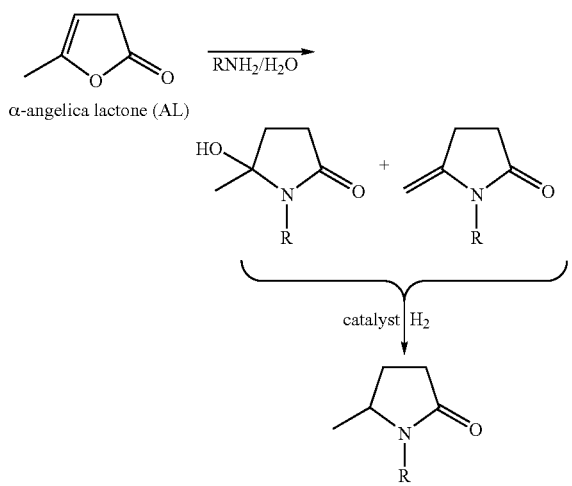

α-angelica lactone (AL)

to produce 5-methyl-N-alkyl-2-pyrrolidone, wherein R is selected from the group consisting of $CH_3$, $C_2H_5$, straight-chain or branched $C_3$ to $C_{30}$ alkyl, and straight-chain or branched $C_3$ to $C_{30}$ alkyl comprising a heteroatom selected from the group consisting of O and N.

2. The process as recited in claim 1, wherein the catalyst is selected from metals selected from the group consisting of nickel, copper, cobalt, iron, rhodium, ruthenium, rhenium, osmium, iridium, platinum, palladium, at least one Raney® metal; compounds thereof; and combinations thereof.

3. The process as recited in claim 2, wherein the catalyst is palladium or compounds thereof.

4. The process as recited in claim 2, wherein the catalyst is supported and the content of the metal in the supported metal catalyst is from 0.1% to 20% by weight.

5. The process as recited in claim 1, wherein the catalyst support is selected from the group consisting of carbon, alumina, silica, silica-alumina, silica-titania, titania, titania-alumina, barium sulfate, calcium carbonate, strontium carbonate, compounds thereof, and combinations thereof.

6. The process as recited in claim 5, wherein the carbon has an ash content, the ash content being less than 5% by weight of the catalyst support, and optionally wherein the carbon has a surface area of more than 200 m²/g.

7. The process as recited in claim 1, wherein the catalyst is augmented with a promoter.

8. The process as recited in claim 1 wherein the inert solvent is water.

9. The process as recited in claim 1, wherein R is selected from the group consisting of $CH_3$, $C_2H_5$, straight-chain or branched $C_3$ to $C_{12}$ alkyl, and straight-chain or branched $C_3$ to $C_{12}$ alkyl comprising a heteroatom selected from the group consisting of O and N.

10. The process as recited in claim 1, wherein $RNH_2$ and α-angelica lactone are in a molar ratio of from about 0.1/1 to about 10/1 at the start of the reaction.

11. The process as recited in claim 10, wherein step (a) is performed at a temperature of from about −25° C. to about 50° C., and step (b) is performed at a temperature of from about 50° C. to about 300° C.

12. The process as recited in claim 10, wherein step (b) is performed at a hydrogen pressure of from about 0.1 MPa to about 20 MPa.

13. The process as recited in claim 4, wherein the supported metal catalyst is selected from the group consisting of palladium on carbon, palladium on calcium carbonate, palladium on barium sulfate, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, rhenium on alumina, ruthenium on carbon, ruthenium on alumina and ruthenium on silica.

14. The process as recited in claim 13, wherein the supported metal catalyst is selected from the group consisting of palladium on carbon, palladium on alumina, palladium on silica, palladium on titania, and combinations thereof.

15. The process as recited in claim 1, wherein R is selected from the group consisting of $CH_3$, $C_2H_5$, straight-chain or branched $C_3$ to $C_{12}$ alkyl, and straight-chain or branched $C_3$ to $C_{12}$ alkyl comprising a heteroatom selected from the group consisting of O and N; the catalyst is supported and the supported catalyst is palladium on carbon or palladium on titania; the temperature of step (a) of the reaction is from about −25° C. to about 50° C., the temperature of step (b) of the reaction is from about 100° C. to 250° C., and the pressure of step (b) of the reaction is from about 1.3 MPa to about 7.6 MPa.

* * * * *